US009448226B2

(12) United States Patent
Dumas et al.

(10) Patent No.: US 9,448,226 B2
(45) Date of Patent: Sep. 20, 2016

(54) METHOD OF TOXICOLOGICAL EVALUATION, METHOD OF TOXICOLOGICAL SCREENING AND ASSOCIATED SYSTEM

(75) Inventors: Marc-Emmanuel Dumas, London (GB); Eric Leclerc, Margny les Compiegne (FR); Laetitia Shintu, Marseilles (FR); Regis Baudoin, Neuilly Plaisance (FR); Cécile Legallais, Villers sous Saint Leu (FR); Pierre Toulhoat, Saint Didier au Mont D'or (FR); Céline Brochot, Cillers sous Saint Leu (FR)

(73) Assignees: Universite Technologie De Compiegne—UTC (FR); Centre National de la Recherche Scientifique (CNRS) (FR); Ecole Normale Superieure De Lyon (FR); Institut National De L'Environnement Industriel Et Des Risques (FR)

( * ) Notice: Subject to any disclaimer, the term of this patent is extended or adjusted under 35 U.S.C. 154(b) by 442 days.

(21) Appl. No.: 13/696,861

(22) PCT Filed: May 12, 2011

(86) PCT No.: PCT/EP2011/057720
§ 371 (c)(1),
(2), (4) Date: Nov. 8, 2012

(87) PCT Pub. No.: WO2011/151148
PCT Pub. Date: Dec. 8, 2011

(65) Prior Publication Data
US 2013/0060550 A1  Mar. 7, 2013

(30) Foreign Application Priority Data

May 12, 2010  (FR) .................... 10 53732

(51) Int. Cl.
| G01N 33/48 | (2006.01) |
| G01N 33/50 | (2006.01) |
| G06F 19/00 | (2011.01) |

(52) U.S. Cl.
CPC ...... *G01N 33/5014* (2013.01); *G01N 33/5041* (2013.01); *G01N 33/5088* (2013.01); *G06F 19/704* (2013.01); *G06F 19/707* (2013.01)

(58) Field of Classification Search
CPC .................................................. G06F 19/704
USPC ........................................................ 702/19
See application file for complete search history.

(56) References Cited

FOREIGN PATENT DOCUMENTS

FR  2946984 A1  12/2010

OTHER PUBLICATIONS

Baudoin et al: "Trends in the development of microfluidic cell biochips for in vitro hepatotoxicity", Toxicology In Vitro, Elsevier Sciencei GB, vol. 21, No. 4, Apr. 10, 2007, pp. 535-544, XP022025268.
Bollard et al: "Metabolic profiling of the effects of D-galactosamine in liver spheroids using (1)H NMR and MAS-NMR spectroscopy.", Chemical Research in Toxicology, vol. 15, No. 11, Nov. 2002, pp. 1351-1359, XP002614421.
Borlon Celine et al: "The usefulness of toxicogenomics for predicting acute skin irritation on in vitro reconstructed human epidermis", Toxicology, vol. 241, No. 3, Nov. 30, 2007. pages 157-166, XP002614420.
Bryan et al., "MetaFIND: A feature analysis tool for metabolomics data", BMC Bioinformatics 2008, 9:470, XP-002614425.
Chrysanthopoulos et al., "Metabolomics for high-resolution monitoring of the cellular physiological state in cell culture engineering", Metabolic Engineering 12 (2010) 212-222.
Daykin et al: "NMR spectroscopy based metabonomics: current technology and applications", Frontiers in Drug Design & Discovery, vol. 2, 2006, pp. 151-173, XP8130643.
De Iorio et al., "Statistical Techniques in Metabolic Profiling", Handbook of Statistical Genetics, Third Edition, © 2007, XP-002614423.
Farkas Dora et al: "In vitro methods to study chemically-induced hepatotoxicity: a literature review.", Current Drug Metabolism, vol. 6, No. 2, Apr. 2005, pp. 111-125, XP8094939.
French Preliminary Search Report for Application No. FR1053732 dated Dec. 16, 2010.

(Continued)

*Primary Examiner* — Jerry Lin
(74) *Attorney, Agent, or Firm* — Lerner, David, Littenberg, Krumholz & Mentlik, LLP

(57) ABSTRACT

The present invention relates to a method of toxicological evaluation of a candidate substance on at least one tissue or organ, characterized in that it comprises the steps of: (a) obtaining a bioartificial tissue or organ by simulation or modelling of the metabolic activity of said tissue or organ by at least one bioreactor; (b) exposure of said bioartificial tissue or organ to said substance; (c) observation of the metabolic response of the bioartificial tissue or organ and acquisition without a priori of an associated multidimensional data set; (d) identification by means of a method of multivariate statistical analysis of the components of the multidimensional data set which are quantitatively correlated with predetermined variables; (e) generation of a predictive model on the basis of the components of the data set that are actually retained; (f) testing of the predictive nature of said model by at least one statistical method of estimating reliability; (g) identification of the metabolic response of the bioartificial tissue or organ in the form of biomarkers associated with the components of the data set that are adopted for the model. The present invention also relates to a method of toxicological screening and to a system for this purpose.

18 Claims, 6 Drawing Sheets

(56) References Cited

OTHER PUBLICATIONS

Inernational Search Report for Application No. PCT/EP2011/057720 dated Jun. 9, 2011.
Majors et al., "NMR Bioreactor development for live in-situ microbial functional analysis", Journal of Magnetic Resonance 192 (2008) 159-166.
Seagle et al., "High-throughput nuclear magnetic resonance metabolomic footprinting for tissue engineering", Tissue Engineering: Part C, vol. 14, No. 2, 2008, XP-002614422.
Thysell et al., "Reliable profile detection in comparative metabolomics", A Journal of Integrative Biology, vol. 11, No. 2, 2007, XP-002614426.
Van Vliet et al: "A novel in vitro metabolomics approach for neurotoxicity testing, proof of principle for methyl mercury chloride and caffeine", Neurotoxicology, Tox Press, Radfield, AR, IN, vol. 29, No. 1, Jan. 1, 2008, pp. 1-12, XP022417840.

US 9,448,226 B2

METHOD OF TOXICOLOGICAL EVALUATION, METHOD OF TOXICOLOGICAL SCREENING AND ASSOCIATED SYSTEM

CROSS REFERENCE TO RELATED APPLICATIONS

The present application is a national phase entry under 35 U.S.C. §371 of International Application No. PCT/EP2011/057720, filed on May 12, 2011, which claims priority from French Patent Application No. 1053732 filed on May 12, 2010, the disclosures of which are incorporated by reference herein.

GENERAL TECHNICAL FIELD

The present invention relates to the field of bioreactors capable of stimulating the organs of living organisms, such as the organs of mammals, in particular human organs.

The invention relates to the application of such bioreactors for the high-throughput screening of toxins on organs thus simulated.

More precisely, it relates to a method for identifying and quantifying endogenous metabolic disturbances related to the presence of toxins, using bioartificial organs.

STATE OF THE ART

Cell cultures represent at present a reliable means for carrying out the toxicological evaluation of chemical or biological substances, i.e., measuring their potential to have harmful effects on a life form.

By conceiving in vitro culture systems of cells of an animal or human tissue or organ (one such system, called a "bioartificial tissue or organ", is for example a synthetic tissue or organ capable of mimicking the biological behavior of the corresponding so-called "natural" tissue or organ, i.e., one taken in its natural environment within the living organism), the reaction of the natural tissue or organ to a substance such as a xenobiotic, a cosmetic, a drug and, more generally, any potentially active principle or agent can be predicted and thus particularly useful in vitro test and analysis models can be developed.

These models are more and more often used in all phases of pharmaceutical research because they are an advantageous alternative to in vivo models, i.e., those involving experiments on animals, against which both economic and ethical pressures exist internationally. Furthermore, the associated costs and the logistics required for animal experimentation, under conditions consistent with the French and European regulations regarding animal welfare and with the recommendations of the relevant health services, can make this technique prohibitive.

Current methods of in vitro toxicological evaluation generally use Petri dishes. These dishes, containing a nutritive medium and placed in an environment favorable to cell growth, are inoculated with cells of the tissue or organ to be simulated. Once they develop, they are brought together with the substance to be tested. The impact on the cells is determined by the sampling and analysis of metabolites, i.e., the products of transformation and/or of degradation of the substance by the cells. This impact can be evaluated qualitatively, a so-called "metabolic disturbance" in the present case, and/or quantitatively by measuring markers, for example, in this case referred to as a "metabolic response."

The term "metabolome" refers to all of the metabolites and other molecules that can be found in a sample.

However, these techniques are far less than satisfactory for determining the toxicity of a particular molecule and predicting its impact on the organ and, more generally, on the living organism. Indeed, it is possible to concentrate the search on only certain predetermined metabolites, at the expense of others that may hold promise. Additionally, an in vitro cell culture is unlikely to reproduce the behavior of a tissue or organ in its natural environment. A cell cultured in vitro is obviously not in the same environment as when it is within the tissue or the organ, a fortiori in the living organism. However, environmental conditions have a direct influence on the biological responses of cells. Typically, a living cell placed in its natural environment plays a part in multiple complex metabolic pathways that are impossible to reproduce in a synthetic culture medium. The biological responses of the cell will thus vary, sometimes considerably, according to whether it is cultured in vitro or whether it is in tissue or the organ and, more generally, in the living organism. Moreover, cells on Petri dishes are cultured under "static" conditions (without circulation of fluids) and not "dynamic" conditions (with circulation of fluids), which are however the only ones likely to reflect the real behavior of an irrigated tissue or organ.

For all these reasons, several recent studies have proposed replacing Petri dishes with bioreactors as a means of culturing cells. These devices reproduce an environment favorable to cell development and organization, similar to that of an animal or human tissue or organ, most often by particular architectures and materials. However, these systems prove relatively incompatible with metabolome analysis techniques.

For example, a system described in the document "NMR bioreactor development for live in-situ microbial functional analysis", *J Magn Reson* 192 (1), 159-166 (2008), by Majors, P. D., McLean, J. S., and Scholten, J. C., proposes a bioreactor located within a nuclear magnetic resonance (NMR) spectrometer. NMR spectrometry makes it possible to easily analyze the bioreactor culture medium, but at the price of very specific constraints. Indeed, the bioreactor precludes microstructures as well as materials other than glass, which limits its possibilities to those of Petri dishes.

Another effort, described in the document "Metabolomics for high-resolution monitoring of the cellular physiological state in cell culture engineering", *Metab Eng* (2009), by Chrysanthopoulos, P. K., Goudar, C. T., and Klapa, M. I., consists of the use of a particular bioreactor to sample and analyze cellular metabolites by gas chromatography-mass spectrometry (GC-MS). This type of spectrometer has proved its effectiveness in identifying substances, and is notably used in airports around the world. However, it requires that the components to be identified are in gas form. Thus, in the Chrysanthopoulos system, the metabolomes present in the bioreactor undergo a so-called "derivatization", i.e., the targeted transformation of certain functional groups of the molecules to make them more volatile, which strongly reduces the number of potentially detectable metabolites because it is restricted to the metabolites targeted by the derivatization.

A third effort, described in the document "High-throughput nuclear magnetic resonance metabolomic footprinting for tissue engineering", *Tissue Eng Part C Methods* 14 (2008), by Seagle, C., Christie, M. A., Winnike, J. H., McClelland, R. E., Ludlow, J. W., O'Connell, T. M., Gamesik, M. P., and MacDonald, J. M., consists of the NMR measurement of metabolites from the culture media of bioartificial organs.

This measurement is followed by a statistical analysis. The idea is to detect specific peaks of the NMR spectrum obtained and thus to "see" the effects of the substance tested. However, this is a rudimentary univariate analysis of the NMR spectrum. Only very strong, highly localized effects can be detected, with most information being lost. Targeted detection remains necessary, with all of its inherent uncertainties, if the close examination of a metabolic disturbance is desired.

Finally, none of this work has a genuine application in toxicological evaluation, with all performing inadequately.

Furthermore, these are not directly applicable to an "inverse" analysis such as toxicological screening, a method for identifying an unknown substance through its known toxicological effects. This screening is possible today only by comparison, i.e., by observing the effects of the substance (in vivo or in vitro) and comparing them with the known effects of various substances until a similar substance is found, with a sufficient degree of confidence.

For all these reasons, in vitro techniques have not yet supplanted in vivo techniques and remain to be improved.

PRESENTATION OF THE INVENTION

The present invention aims to resolve these difficulties by proposing a method of toxicological evaluation on bioartificial organs or tissues that perfectly simulate real organs, and proposing a novel approach to the analysis of the metabolic response.

An additional aim of the invention is to arrive at this objective while proposing a method that is faster, less expensive to implement and more reliable, providing results that are perfectly reproducible and much more easily applied.

The present invention thus relates to a method of toxicological evaluation of a candidate substance on at least one tissue or organ, characterized in that it comprises the steps of:

(a) obtaining a bioartificial tissue or organ by simulation or modeling of the metabolic activity of said tissue or organ by at least one bioreactor;

(b) exposure of said bioartificial tissue or organ to said substance;

(c) observation of the metabolic response of the bioartificial tissue or organ and acquisition without a priori an associated multidimensional data set;

(d) identification by means of a method of multivariate statistical analysis of the components of the multidimensional data set which are quantitatively correlated with predetermined variables;

(e) generation of a predictive model on the basis of the components of the data set actually selected;

(f) testing of the predictive nature of said model by at least one statistical method of estimating reliability;

(g) identification of the metabolic response of the bioartificial tissue or organ in the form of biomarkers associated with the components of the data set selected for the model.

The standard evaluation by sampling toxic substances and their residues (i.e., xenobiotic metabolites), a so-called direct evaluation, is carried out by enzymatic methods or by mass spectrometry coupled or not with a chromatographic separation method. These methods are referred to as targeted or "with a priori" methods because they rely upon the detection of substances for which a specific detection protocol is used. On the other hand, these methods are inappropriate for the detection and identification of markers of the effects of an unknown substance, as explained above.

In order to respond to these problems, the invention proposes to study the indirect consequences of the exposure of bioartificial organs to a toxic substance, by characterizing the metabolic signature of the response to this substance.

The invention is focused on the use of so-called "non-targeted" methods such as nuclear magnetic resonance (NMR) spectroscopy or mass spectrometry (MS), coupled or not with chromatography, in order to detect the largest possible number of endogenous metabolites. In order to identify an overall response on the scale of the metabolism, these various parallel measurements are then analyzed by multidimensional statistics. These analyses aim in fact to "explain" the experimental parameters using thousands of measured variables, and to deduce from them a predictive model. It is indeed possible to use supervised pattern recognition techniques such as discriminant analysis, partial least squares (PLS) regression, artificial neural networks, etc.

According to other advantageous and nonrestrictive characteristics:

the method of multivariate analysis used in step (d) is a partial least squares discriminant analysis (PLS-DA);

step (d) is preceded by a step (d1) of locating and eliminating aberrant points in said multidimensional data set;

step (d1) comprises an unsupervised principal component analysis (PCA);

one of the statistical methods for estimating reliability used in step (d) is cross-validation;

one of the statistical methods for estimating reliability used in step (d) is validation by the null hypothesis;

one of the statistical methods for estimating reliability used in step (d) comprises the calculation of the area under a receiver operating characteristic (ROC) curve;

the predetermined variables used in step (d) are selected from the culture conditions, the cell type of the bioartificial tissue or organ, the type of said substance, and its amount;

step (c) is carried out by at least one analytical chemistry technique selected from the techniques of the group comprising proton NMR spectroscopy, carbon NMR spectroscopy, mass spectrometry, gas chromatography, liquid phase chromatography and multiplexed detection methods;

step (c) is carried out in culture medium leaving the bioreactor in order to observe the extracellular metabolic response;

step (c) is carried out on cell pellets in order to observe the intracellular endogenous metabolic response;

the method further comprises a step (h) of obtaining a specific toxicity signature of said substance from the list of biomarkers obtained in step (g);

the method further comprises a step (i) in which a bank of markers and/or toxicity signatures is created using the information obtained during the preceding steps.

The present invention also aims to enable reliable high-throughput toxicological screening, according to a second aspect.

The present invention thus further relates to a method of toxicological screening of a candidate substance on at least one tissue or organ, characterized in that it comprises the steps of:

(a) obtaining a bioartificial tissue or organ by simulation or modeling of the metabolic activity of said tissue or organ by at least one bioreactor;

(b) exposure of said bioartificial tissue or organ to said substance;

(c) observation of the metabolic response of the bioartificial tissue or organ and acquisition without a priori an associated multidimensional data set;

(d) identification by means of a method of multivariate statistical analysis of the components of the multidimensional data set which are quantitatively correlated with predetermined variables;

(e) generation of a predictive model on the basis of the components of the data set actually selected;

(f) testing of the predictive nature of said model by at least one statistical method of estimating reliability;

(g) identification of the metabolic response of the bioartificial tissue or organ in the form of biomarkers associated with the components of the data set selected for the model;

(h) obtaining a specific toxicity signature of said substance from the list of biomarkers obtained in step (g);

(i) comparison of the biomarkers and/or the specific toxicity signature with a bank of markers and/or toxicity signatures, so as to identify said substance.

According to other advantageous and nonrestrictive characteristics:

said bank of markers and/or toxicity signatures were established by the implementation of at least one method according to the first aspect of the invention.

This high-throughput screening of substances is made possible by the constitution of a data base or bank compiling the results of previous experiments. This application opens the door to the analytical screening of substances whose toxicity would never have been shown, by rapid, immediate and statistical comparison with reference substances whose toxicity signature, i.e., a specific representation of the metabolic response, is known.

Finally, the invention relates to systems, one comprising at least one bioreactor, means of data processing and a device for detecting biomarkers, characterized in that it is able to implement a method of toxicological evaluation according to the first aspect of the invention, and the other further comprising means of data storage, characterized in that it is able to implement a method of toxicological screening according to the second aspect of the invention.

PRESENTATION OF FIGURES

Other characteristics and advantages of the present invention will become evident upon consideration of the description followed by a preferential embodiment. This description will be given in reference to the appended drawings in which.

Figure 4A:
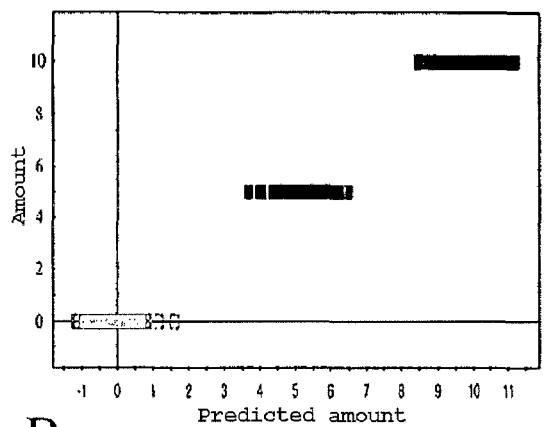
Figure 4B:
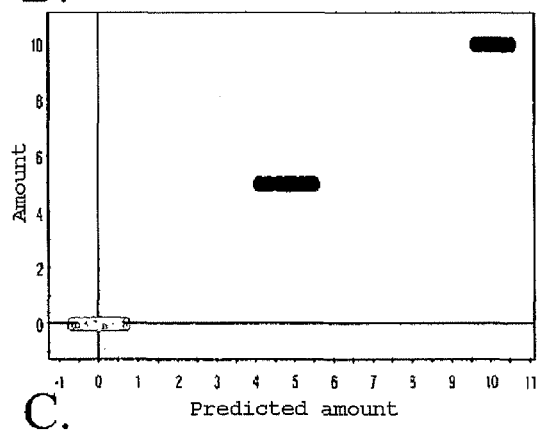
Figure 4C:
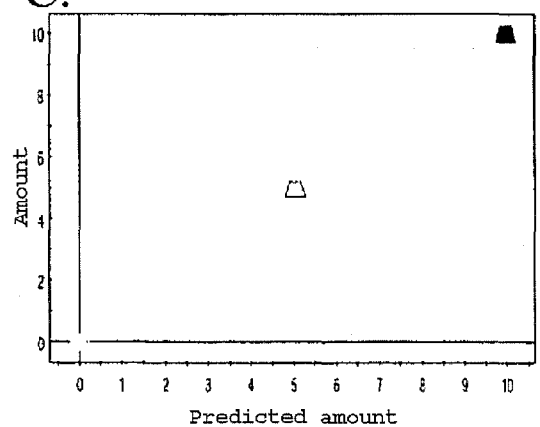
Figure 5A:
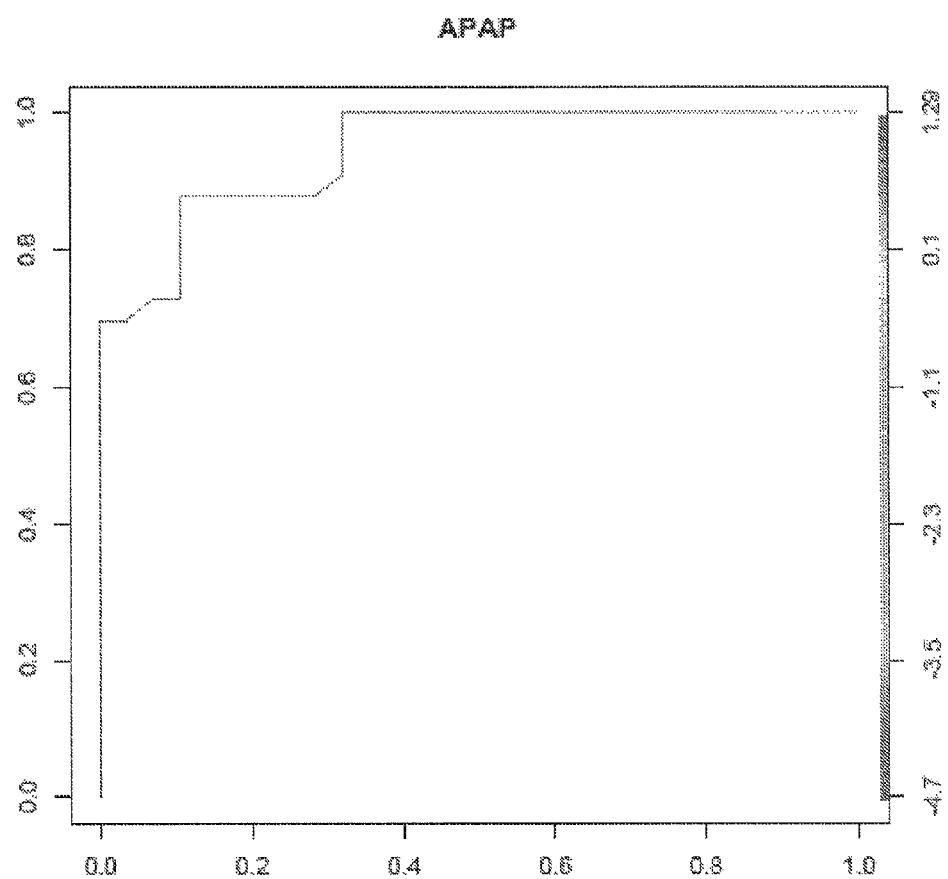
Figure 5B:
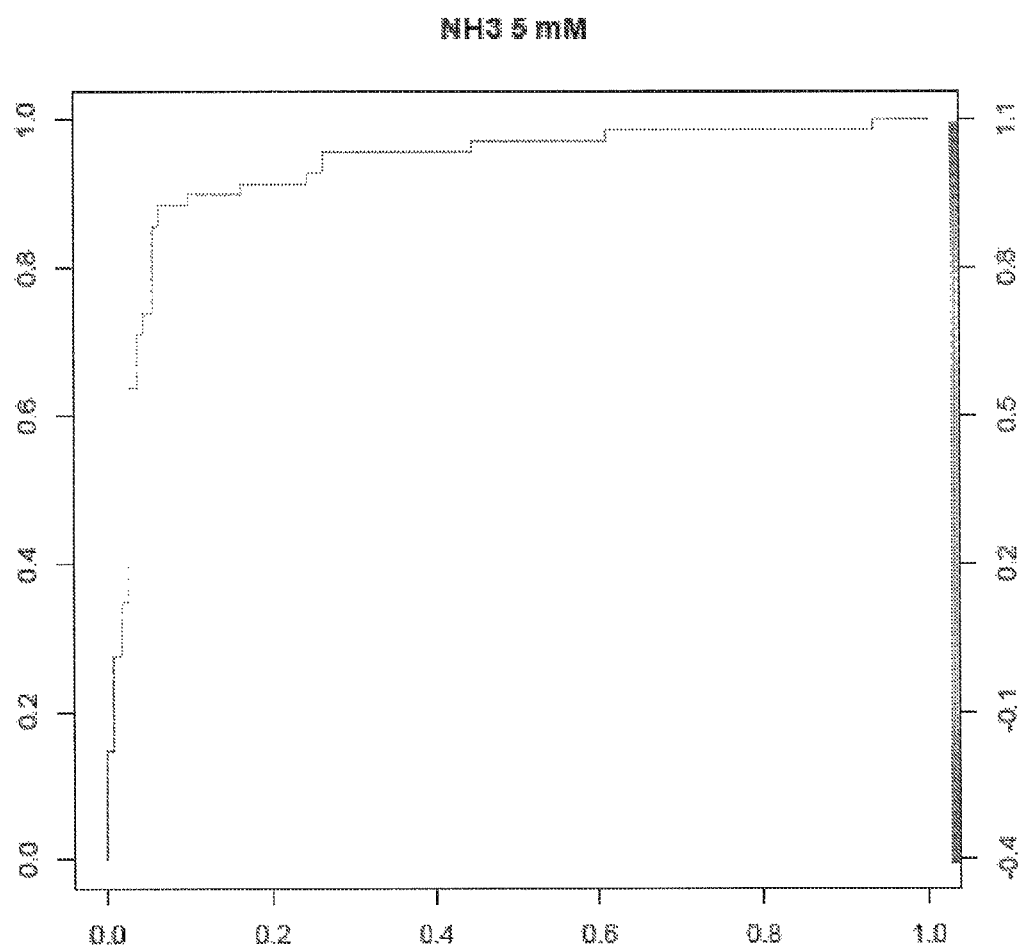

FIGS. 4a-c are three graphs illustrating the result of a third experiment comparing a metabolic response to various amounts of a same xenobiotic by $^1$H NMR analysis and PLS regression;

FIGS. 5a-b are two examples of receiver operating characteristic curves used in one embodiment of the method of toxicological evaluation according to the invention.

DETAILED DESCRIPTION

Toxicological Evaluation

The method of toxicological evaluation according to the first aspect of the invention begins with a step of obtaining an artificial tissue or organ, on which the substance will be tested. To that end, bioreactors are used. These comprise advantageously a culture chamber comprising a microstructured upper wall and lower wall promoting cell development, a fluid entry point and a fluid exit point to allow the passage of a nutritive fluid necessary for cell development and growth and in the long term the exposure to the substance whose toxicological properties are under study. Such bioreactors are described in detail in the patent application FR0954288 filed on Jun. 23, 2009, to which reference is made herein. The invention is not however limited to this type of bioreactor in particular.

A bioreactor's microstructures make possible the development of bioartificial tissues or organs that have an elaborate cellular structure consistent with reality. Growth is accelerated and autonomous. Bioreactors can be easily assembled in series or parallel. It is thus possible to culture one after the other various cell families, which together simulate an organ. Living organs are indeed highly complex systems that shelter in general one principal cell type, more than many others, whose presence proves essential. For example, in the case of the liver, 80% of the cells are what are called hepatocytes, but also found are endothelial cells, Kuppfer cells, Ito cells, hepatic lymphocytes, etc.

More simply, it is also possible to aim rather at a structural reproduction of the function of the organ, and at modeling it from that. The case of the kidney can be cited, for example.

Furthermore, the dynamic operation of the bioreactor makes possible, beyond better simulation of the tissue or organ, exposure to a substance and then easy recovery of the metabolic response of the cells cultured in the bioreactor's outflow connector. In this case, the so-called extracellular metabolic response is observed. Alternatively, it can be useful to observe the endogenous metabolic response, i.e., within the cells. In this case the metabolic response is recovered directly on the cell pellets.

The bioartificial tissues or organs are thus cultured to maturity and then exposed to a substance to be tested. After a predetermined time according to the test protocol, the samples are recovered, whether from the outflow or from within the cells.

The samples are prepared for observation. As explained, the so-called "non-targeted" methods of NMR or mass spectrometry are particularly preferred. These methods, as well as many others, are widely used in analytical chemistry and are known to the person skilled in the art. An NMR spectrum of a sample of culture medium of a bioartificial organ enables for example acquisition in parallel and without a priori signals of several dozens or even hundreds of metabolites, i.e., multidimensional acquisition. NMR is a method of spectroscopy applied to a particle or to a set of particles. In particular, NMR techniques based on atoms characteristic of organic molecules, such as hydrogen or carbon, apply particularly to the invention.

Acquisition "without a priori" a data set associated with the metabolic response is understood to mean acquisition of all data associated with any metabolic response, and not only data associated with "expected" elements of a metabolic response. No hypothesis concerning the metabolites involved in the biological or toxicological response of interest is to be made. In other words, an acquisition without a priori a data set associated with the metabolic response is an acquisition which incorporates data corresponding to unknown metabolites. A without a priori approach is fundamentally different than the targeted approach (targeted metabolomics) in which all that does not correspond to the targeted metabolites is ignored.

As explained above, the use of NMR or other spectroscopic methods, among others, enables a without a priori acquisition, in contrast with the use for example of a DNA chip, which limits to the acquisition of data associated with the expression only of genes comprised by the chip, in other words with a partial metabolic response. The multidimensional statistics then make it possible to identify the metabolic signals significantly affected and in which proportions. Consequently, the without a priori approach is highly advantageous in terms of discovering new markers associated with this toxicological response. In the targeted approach, the potential in terms of discovery of new markers is nonexistent.

In the preferred embodiment described, $^1$H NMR spectroscopy (proton NMR, which makes it possible to detect hydrogen atoms) was used to carry out a series of tests. These tests involved two cell lines and three potentially toxic substances, with the two lines being optionally in coculture. These cells are in one case HEPG2/C3A cells, or simply C3A, human hepatocyte cells, and in the other case Madin-Darby canine kidney (MDCK) cells. It will be noted that the invention is by no means limited to bioartificial livers and kidneys, and that the person skilled in the art will be able to transpose the invention to any type of bioartificial organ that can be simulated or modeled in a bioreactor. In particular, mention may be made of the pancreas, the heart, the testicles, parts of the brain, etc.

The xenobiotics to which the cells used in the tests were exposed are ammonia ($NH_3$), dimethyl sulfoxide (DMSO) and N-acetyl-para-aminophenol (APAP), more commonly known by the name paracetamol. These three substances at high doses are known to have harmful effects on the liver.

The medium samples are, for example, prepared using 350 µl of medium, mixed with 200 µl of 0.9 g/l saline solution composed of 90% water ($H_2O$) and 10% heavy water ($D_2O$), for the purpose of calibration. The 550 µl of solution is then transferred to an NMR analysis tube.

NMR is acquired at a frequency of 700 MHz by using a proton probe. A $^1$D NMR spectrum is recorded using presaturation of the resonance of the water according to the following sequence: $T_{rd}$-$P_{90}$-$t_1$-$P_{90}$-$t_m$-$P_{90}$-$T_{aq}$. $T_{rd}$ represents a delay of 2 seconds during which the resonance of the water is selectively irradiated, $P_{90}$ is a 90° pulse of radio frequency and $t_1$ corresponds to a delay of 3 µs. The resonance of the water is irradiated a second time during the mixing time ($t_m$=100 ms) and an acquisition time of 1.95 s. For each sample, 128 interferograms are accumulated in order to increase the signal-to-noise ratio. These interferograms are multiplied by an exponential function corresponding to a 0.3 Hz enlarging of the line. Before obtaining a Fourier transform, the width of the interferogram is doubled by adding null points at the end of the interferogram, in order not to degrade the resolution of the spectrum. The scale in the horizontal dimension corresponds to the $^1$H chemical shifts. It extends over a window of 10 ppm around the resonance of water. The scale in the vertical dimension corresponds to resonance intensity which is proportional to the number of protons present for a chemical group of each molecule of the sample. The spectra are then phased and a linear correction of the baseline is carried out, before calibration on the signal of the beta anomer of glucose at 5.23 ppm. The area between 4.67 ppm and 5 ppm around the residual signal of water is suppressed for better visibility, and the spectra are exported as a multidimensional data set.

Figure 1:
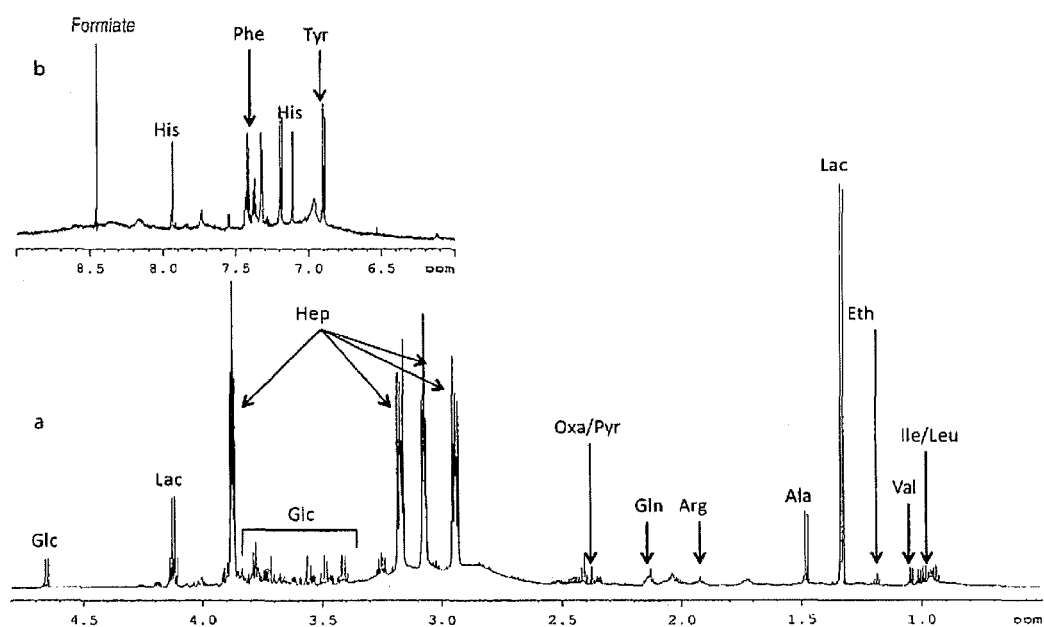
FIG. 1 is an example of a $^1$H NMR (proton NMR) spectrum.

FIG. 1 shows an example of the $^1$H NMR spectrum of a sample of culture supernatant of C3A cells exposed to ammonia (25 µl/min, 10 mM $NH_3$). The region comprising the aromatic resonances (between 6.5 and 10 ppm) was increased. The peaks of the principal metabolites are annotated as examples. Key: His: histidine, Phe: phenylalanine, Tyr: tyrosine, Glc: glucose, Lac: lactate, Oxa: oxaloacetate, Pyr: pyruvate, Gln: Glycine, Arg: Arginine, Ala: alanine, Eth: ethanol, Val: valine, Leu: leucine, Ile: isoleucine.

The statistical analysis consists first of an unsupervised principal components analysis in order to locate aberrant points in the multidimensional data set. The principal components analysis makes it possible to compress the 40,000 redundant NMR present in the data set in a new orthonormal reference, with each axis representing a principal component of the variance of the data set, which is thus multidimensional. A so-called supervised multivariate statistical analysis is then carried out in order to discriminate culture conditions or groups of doses and to identify the metabolic signatures specific to the toxicological effects. This supervised analysis is principally carried out using partial least squares regression, through partial least squares discriminant analysis (PLS-DA), without however being limited to it. A PLS regression, just like a linear regression, makes it possible to identify the components of the data set (explanatory variables, X) that are quantitatively correlated with the non-explanatory variable (Y), whether the culture conditions, the cell type of the bioartificial organ, the type of treatment administered or the treatment dose. Artificial neural network structures can also be programmed to carry out this multivariate analysis.

In order to test the predictive nature of the supervised models (PLS models in the present case), several strategies are used. Once the discrimination or regression rule is generated, the estimate of the errors associated with this rule provides a tool for its validation. Cross-validation makes it possible to understand the robustness of the discrimination or regression method, without having recourse to a set of individuals to be tested, and to clarify the incidence of a restricted number of measurements on the model. Each data set is randomly subdivided into several parts. The sub-parts are then iteratively used either to calibrate the model or to be subjected to a prediction of the model. For each cross-validation iteration part of the data set is removed; the rest of the data set is used to calibrate the model. Once the decision or regression rule is generated with the calibration samples, the coordinates of the set of test samples are then calculated, which makes it possible to assign a prediction (dose or group) to these test samples and to calculate the prediction error. The prediction error can appear in the form of a confusion matrix making it possible to calculate an error rate (or a good prediction rate) or in the form of the calculation of a coefficient of error, typically Q2.

Subsequently, it is also possible to test the robustness of the model by randomly generating a series of data sets for which the non-explanatory variable Y has been permuted. There is thus no longer a relationship between the non-explanatory variable Y and the explanatory variables X, which corresponds in statistics to validation by the null hypothesis. Typically, a series of several hundred models according to the null hypothesis is generated and their robustness is evaluated by cross-validation. It is then possible to show that the more random the models are the more difficult it is to construct a predictive model. It can then be shown that the initial model is significantly different from the population of random models according to the null hypothesis, which all the more strongly validates the initial model.

According to a particularly advantageous embodiment, receiver operating characteristic (ROC) curves can be used. These curves, known to the person skilled in the art, are used to evaluate the performance of a binary classifier. A ROC curve gives the rate of correct classifications in a group (true positive rate) as a function of the number of incorrect classifications (false positive rate) for this same group. The curve is thus included in a square with a side of 1, and necessarily passes through (0,0) and (1,1). To apply it to the models generated by the invention, positive or negative samples will be tested and classified according to the accuracy or inaccuracy of the prediction.

In the case of a perfect model, the ROC curve passes through (0,1). In the case of a model that does not give better results than random selection, the ROC curve would be the line y=x. In the first case the integral between 0 and 1 of the curve is 1, and in the second case ½.

The area under the curve (AUC), which corresponds mathematically to the probability that the model is right during a prediction, will thus be measured. This value will thus be a very good indicator of the validity of a model.

When the model has proven its validity, a biomarker identification step follows. This step makes it possible to better translate the reality of the metabolic response since it makes it possible to find the metabolites associated with the components of the data set selected for the model, i.e., the most characteristic of exposure to the toxic substance. This step is carried out, for example, by having a professional read the associated peaks on the NMR spectrum.

Advantageously, a specific toxicity signature of said substance is deduced from these biomarkers. There is no characteristic format for a toxicity signature, which may quite simply comprise a list of metabolites, each characterized by a correlation coefficient (direction of the variation of metabolite concentration in relation to a control situation). It can also be a graphical signature, for example a simplified spectrum, reduced to the detected peaks deemed essential by the multivariate analysis. The invention is not limited to a toxicity signature in particular.

Still more advantageously, these signatures are stored in a database in order to constitute a signature bank. A marker bank can be envisaged, in which each biomarker is referenced by the list of substances in the case in which it was involved. Such a bank could be very useful for another aspect of the invention, which will be described low.

Experimental Results

Four experiments were carried out according to the embodiment described above in order to show the effectiveness of the method of toxicological evaluation according to the invention:

1. Comparison of the metabolic signatures between the bioartificial organs and Petri dishes;
2. Comparison of the metabolic signatures of various bioartificial organs (liver C3A, kidney MDCK and liver-kidney coculture);
3. Comparison of the specific metabolic responses of the various bioartificial organs (liver C3A, kidney MDCK and liver-kidney coculture) to the same substance ($NH_3$);
4. Comparison of the specific metabolic responses of a bioartificial liver to various substances ($NH_3$, DMSO, APAP).

The results of Experiments 1 to 4 are presented in Tables 1 to 4, respectively.

Figure 2:
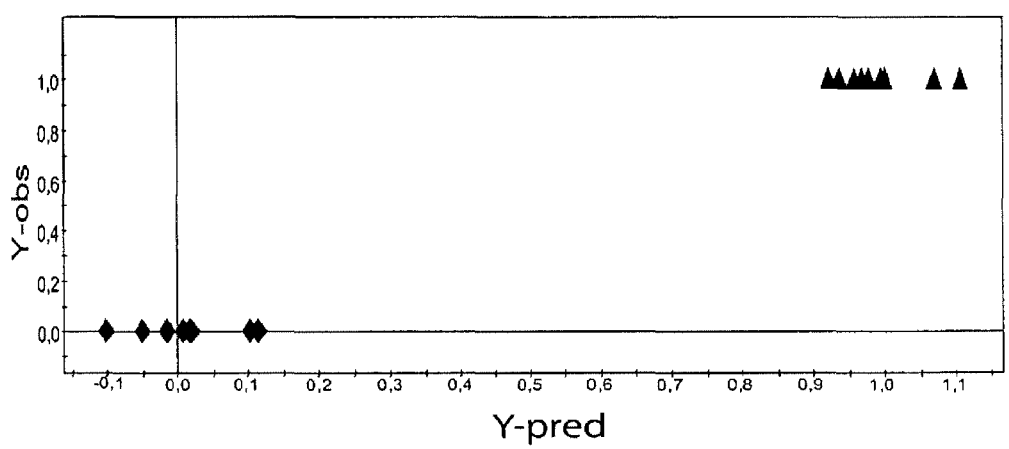
FIG. 2 is a graph illustrating the result of a first experiment comparing a method of toxicological evaluation according to the invention and a similar method that uses Petri dishes using modeling of $^1$H NMR spectra by partial least squares regression.

First, the metabolic signature of a culture of bioartificial organs in a bioreactor was compared to that of a standard culture in Petri dishes. The metabolism of C3A bioartificial livers in a bioreactor was compared to that of C3A cells in standard culture in Petri dishes. Two partial least squares discriminant analyses (PLS-DA) were constructed in order to compare the culture of C3A cells in Petri dishes to that of C3A cells in a bioreactor with an optimal flow rate of 10 μl/min (FIG. 2). The PLS-DA models show a clear discrimination between cells cultured in Petri dishes and cells within the bioreactors, demonstrating an endogenous metabolic signature of bioartificial organs, directly connected to culture in bioreactors. The coefficients of each PLS model were analyzed in order to locate the metabolites significantly affected by culture in a bioreactor.

The comparison of the lists of metabolites for each bioreactor culture condition (Table 1) show that a bioartificial organ has a unique and characteristic metabolic response, related to the cellular physiology of a three-dimensional organ, with circulation of the culture medium around the cells, which a cell culture in a Petri dish does not reproduce.

FIG. 2 also illustrates this result by demonstrating that Petri dishes and bioreactors have different metabolic signatures. The graph of the cloud of individuals shows a significant difference between the two families.

TABLE 1

| Metabolite | Sign of the correlation in the bioreactor in relation to Petri dishes |
|---|---|
| Lactate | − |
| Formate | − |
| Glucose | + |
| Glycine | + |
| Pyruvate | + |
| Oxaloacetate | + |
| Alpha-hydroxybutyrate | + |

Figure 3:
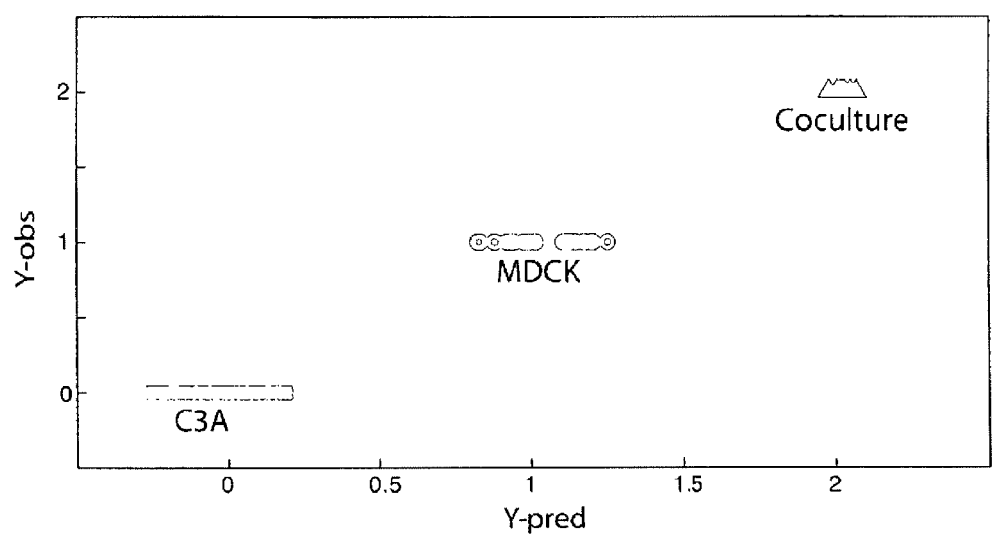
FIG. 3 is a graph illustrating the result of a second experiment comparing various cell types by $^1$H NMR and PLS regression.

Second, the metabolic signatures of the various bioartificial organs are compared, more precisely in the case of liver (C3A cells), kidney (MDCK cells) and liver-kidney (C3A/MDCK) coculture in the complete absence of treatment. Three partial least squares discriminant analyses (PLS-DA) were constructed in order to compare the C3A bioartificial liver cultures with the MDCK bioartificial kidney cultures and C3A/MDCK cocultures with an optimal flow rate of 10 μl/min (FIG. 3). The PLS-DA models show a clear segregation between the three types of organs. The coefficients of each PLS model were analyzed in order to locate the metabolites significantly different between the bioartificial organs.

The comparison of the lists of metabolites for each bioartificial organ reveals a unique metabolic signature thus demonstrating the presence of an endogenous metabolism specific to each type of bioartificial organ, directly connected to the physiological function of this organ in the whole organism (Table 2). This is confirmed by FIG. 3.

TABLE 2

| Metabolite | Sign of the C3A correlation | Sign of the MDCK correlation | Sign of the C3A-MDCK coculture |
|---|---|---|---|
| Glycine | | − | |
| Glutamate | | | + |
| Succinate | + | | + |
| Oxaloacetate | | − | |
| Pyruvate | | − | |
| Pyroglutamate | | + | |
| Alanine | + | | + |
| Valine | + | | |
| Leucine | + | | |
| Isoleucine | + | | |

Third, the metabolic responses of the various organs to various exposures to $NH_3$ were studied. Three amounts of $NH_3$ were administered (0 mM, 5 mM and 10 mM) to each type of bioartificial organ. In order to increase the robustness of the system and to avoid metabolic variations related to culture density, these were replicated several times with various densities from 200,000 to 1,000,000 cells (FIG. 4a-c, Table 3). A multidimensional partial least squares (PLS) regression model was constructed in order to identify a quantitative relationship between the amount of $NH_3$ administered and the metabolic response for each type of bioartificial organ. The result is three PLS models specific to each organ type: liver (C3A, FIG. 3A), kidney (MDCK, FIG. 3B) and coculture (C3A/MDCK, FIG. 3C).

The PLS regression models show a quantitative dose-response relationship, demonstrating an indirect endogenous metabolic response quantitatively linked to the amount of $NH_3$ administered. The coefficients of each PLS model were analyzed in order to locate the metabolites significantly affected by the amount of $NH_3$. The comparison of the lists of metabolites for each bioartificial organ shows that each one has a unique and characteristic metabolic response related to the cellular physiology and toxicology specific to each organ.

Table 3 presents for each metabolite the sign of the variation of its concentration when the amount of $NH_3$ to which the bioartificial organ is exposed increases.

TABLE 3

| Organ | Metabolites | Variation |
|---|---|---|
| Bioartificial liver (C3A cells) | Alanine | + |
| | Valine | + |
| | Isoleucine | + |
| | Leucine | + |
| | Alpha-keto-methylvalerate | − |
| | Alpha-keto-isovalerate | − |
| | Succinate | + |
| Bioartificial kidney (MDCK cells) | Glutamine | − |
| | Oxaloacetate | − |
| | Pyruvate | − |
| | Pyroglutamate | + |
| | Lysine | − |
| | Unknown | − |
| C3A-MDCK coculture | Glutamine | + |
| | Succinate | + |
| | Glutamate | + |
| | Alpha-hydroxyisobutyrate | + |
| | Valine | + |
| | Lysine | + |
| | Ornithine | − |

Fourth, the specific metabolic responses of bioartificial livers exposed to various toxins were characterized (Table 4). Several toxic substances ($NH_3$ (0.5 and 10 mM); DMSO (0%, 1%, 2%, 4%); APAP (0.1 mM)) were administered to bioartificial livers comprised of C3A cells. In the case of treatment with APAP, the response of the bioartificial liver was compared with that of liver cells in culture in Petri dishes. For each exposure, a multidimensional partial least squares (PLS) regression model was constructed in order to identify a quantitative relationship between the amount of each substance administered and the metabolic response of each type of bioartificial organ. The result is four PLS models specific to each treatment type: $NH_3$ on C3A bioartificial liver, DMSO on C3A bioartificial liver, APAP on C3A bioartificial liver and, finally, APAP on C3A cell culture in Petri dishes. The PLS regression models show a quantitative dose-response relationship, demonstrating an indirect endogenous metabolic response of bioartificial livers quantitatively linked to each treatment administered. The coefficients of each PLS model were analyzed in order to locate the hepatic endogenous metabolites significantly affected by one treatment or another. The comparison of the lists of metabolites for each treatment shows that the bioartificial liver has a unique and characteristic metabolic response to each toxic molecule administered (Table 4). This table presents for each metabolite the sign of the variation of its concentration (in brackets) when the amount of xenobiotic in the experiment increases.

Each of these results is a toxicity signature of the xenobiotic, which is unique to it.

TABLE 4

| $NH_3$ | DMSO | APAP | Petri APAP |
|---|---|---|---|
| Alanine (+) | | | |
| | Glucose (+) | | |
| Valine (+) | | | |
| Isoleucine (+) | | Isoleucine (−) | Isoleucine (−) |
| Leucine (+) | | | Leucine (−) |
| Succinate (+) | | Succinate (−) | |
| Alpha-keto-methylvalerate (−) | Alpha-keto-methylvalerate (−) | | |
| Alpha-keto-isovalerate (−) | Alpha-keto-isovalerate (−) | | |
| | Phenylalanine (+) | | Phenylalanine (−) |
| | Tyrosine (+) | | |
| | Lactate (−) | | |
| | | Unknown (−) | |
| | | Acetate (+) | |
| | | Tyrosine (+) | |
| | | Pyruvate/oxaloacetate (−) | |
| | | | Ethanol (−) |
| | | | Glutamate (−) |
| | | | Lysine (−) |
| | | | Arginine (−) |

In addition to these four experiments, ROC curves were calculated for several models in order to evaluate their performances. The toxicity predictions, for example, were made for a set exposed to 10 mM APAP and to 5 mM $NH_3$. The respective ROC curves obtained are presented in FIGS. 5a and 5b.

The AUC is 0.943723 and 0.9335968, respectively, with a confidence of almost 95%. A model for evaluating the toxicity of 10 mM $NH_3$ has an AUC of 0.9994318 (99.94% confidence).

The performances of the models are thus completely satisfactory.

Toxicological Screening

According to a second aspect the invention proposes a method of toxicological screening.

The idea is to constitute a base of signatures by comparison with which a xenobiotic can be very quickly identified. Advantageously, each time a new substance is evaluated with the method according to the first aspect, its signature is added to a database. Over time an increasingly complete database emerges.

When the goal is to identify an unknown substance, the first step is to proceed with all of the steps of the toxicological evaluation in order to obtain its toxicity signature. Next, signatures comparable to the signature of the unknown substance are searched in the database and identified. Advantageously, a tolerance threshold is set by the user. A very low tolerance level increases the probability of not detecting a substance that is nevertheless known, but ensures a high degree of confidence if the substance is indeed identified. A lower tolerance level makes it possible to propose several solutions, which are left for the user to select from. Alternatively, it is not the signatures which are compared but the lists of biomarkers detected, or directly the spectra.

If a substance has already been encountered, this method makes it possible to identify it with great certainty in only a few minutes, opening prospects for high-throughput screening. Currently, the only methods for identifying an unknown substance consist of a succession of chemical tests selected by the user, making it necessary to construct and spend time and resources on hypotheses.

Systems

According to a final aspect, the invention proposes systems that implement the method of toxicological evaluation according to the first aspect of the invention, or that implement the method of toxicological screening according to the second aspect of the invention. These systems comprise at least one bioreactor, means of data processing and a device for detecting biomarkers.

The system intended for toxicological screening further comprises means of data storage on which can be stored the database containing, for example, the signatures of known xenobiotics.

The invention claimed is:

1. A method of toxicological evaluation of a candidate substance on at least one tissue or organ, comprising the steps of:
   (a) obtaining a bioartificial tissue or organ by simulation or modeling of the metabolic activity of said tissue or organ by at least one bioreactor;
   (b) exposing said bioartificial tissue or organ to said substance by introducing said substance inside the at least one bioreactor during said at least one bioreactor functioning;
   (c) observing the metabolic response of the bioartificial tissue or organ and acquiring, without an a priori method, an associated multidimensional data set;
   (d) identifying by means of a method of multivariate statistical analysis the components of the multidimensional data set which are quantitatively correlated with predetermined variables;
   (e) generating a predictive model, consisting of a function between the predetermined variables and the components of the data set actually selected, on the basis of the components of the data set actually selected;
   (f) testing of the predictive nature of said model by at least one statistical method of estimating reliability; and
   (g) identifying the metabolic response of the bioartificial tissue or organ in the form of biomarkers associated with the components of the data set selected for the model.

2. The method of claim 1 wherein the method of multivariate analysis used in step (d) is a partial least squares discriminant analysis (PLS-DA).

3. The method of claim 1 wherein step (d) is preceded by a step (d1) of locating and eliminating aberrant points in said multidimensional data set.

4. The method of claim 3 wherein step (d1) comprises an unsupervised principal component analysis (PCA).

5. The method of claim 1 wherein one of the statistical methods for estimating reliability used in step (d) is cross-validation.

6. The method of claim 1 wherein one of the statistical methods for estimating reliability used in step (d) is validation by the null hypothesis.

7. The method of claim 1 wherein one of the statistical methods for estimating reliability used in step (d) comprises the calculation of the area under a receiver operating characteristic (ROC) curve.

8. The method of claim 1 wherein the predetermined variables used in step (d) are selected from the culture conditions, the cell type of the bioartificial tissue or organ, the type of said substance, and its amount.

9. The method of claim 1 wherein step (c) is carried out by at least one analytical chemistry technique selected from the techniques of the group comprising proton NMR spectroscopy, carbon NMR spectroscopy, mass spectrometry, gas chromatography, liquid chromatography and multiplexed detection methods.

10. The method of claim 1 wherein step (c) is carried out in the culture medium exiting the bioreactor in order to observe the extracellular metabolic response.

11. The method of claim 1 wherein step (c) is carried out on cell pellets in order to observe the intracellular endogenous metabolic response.

12. The method of claim 1 further comprising a step (h) of obtaining a specific toxicity signature of said substance from the list of biomarkers obtained in step (g).

13. The method of claim 1 further comprising a step (i) in which a bank of markers and/or toxicity signatures is created using the information obtained during the preceding steps.

14. A method of toxicological screening of a candidate substance on at least one tissue or organ, comprising the steps of:
   (a) obtaining a bioartificial tissue or organ by simulation or modeling of the metabolic activity of said tissue or organ by at least one bioreactor;
   (b) exposing said bioartificial tissue or organ to said substance by introducing said substance inside the at least one bioreactor during said at least one bioreactor functioning;
   (c) observing the metabolic response of the bioartificial tissue or organ and acquiring, without an a priori method, an associated multidimensional data set;
   (d) identifying by means of a method of multivariate statistical analysis the components of the multidimensional data set which are quantitatively correlated with predetermined variables;
   (e) generating a predictive model, consisting of a function between the predetermined variables and the components of the data set actually selected, on the basis of the components of the data set actually selected;
   (f) testing of the predictive nature of said model by at least one statistical method of estimating reliability;

(g) identifying the metabolic response of the bioartificial tissue or organ in the form of biomarkers associated with the components of the data set selected for the model;
(h) obtaining a specific toxicity signature of said substance from the list of biomarkers obtained in step (g);
(i) comparing the biomarkers and/or the specific toxicity signature with a bank of markers and/or toxicity signatures, so as to identify said substance.

15. A method of toxicological screening of a candidate substance on at least one tissue or organ, comprising the steps of:
(a) obtaining a bioartificial tissue or organ by simulation or modeling of the metabolic activity of said tissue or organ by at least one bioreactor;
(b) exposing said bioartificial tissue or organ to said substance by introducing said substance inside the at least one bioreactor during said at least one bioreactor functioning;
(c) observing the metabolic response of the bioartificial tissue or organ and acquiring, without an a priori method, an associated multidimensional data set;
(d) identifying by means of a method of multivariate statistical analysis the components of the multidimensional data set which are quantitatively correlated with predetermined variables;
(e) generating a predictive model, consisting of a function between the predetermined variables and the components of the data set actually selected, on the basis of the components of the data set actually selected;
(f) testing of the predictive nature of said model by at least one statistical method of estimating reliability;
(g) identifying the metabolic response of the bioartificial tissue or organ in the form of biomarkers associated with the components of the data set selected for the model;
(h) obtaining a specific toxicity signature of said substance from the list of biomarkers obtained in step (g);
(i) comparing the biomarkers and/or the specific toxicity signature with a bank of markers and/or toxicity signatures, so as to identify said substance wherein said bank of markers and/or toxicity signatures is established by the implementation of the method according to claim 13.

16. A system comprising at least one bioreactor, means of data processing and a device for detecting biomarkers, wherein the system is able to implement the method of toxicological evaluation according to claim 1.

17. A system comprising at least one bioreactor, means of data processing, means of data storage, and a device for detecting biomarkers, wherein the system is able to implement the method of toxicological screening according to claim 14.

18. A system comprising at least one bioreactor, means of data processing, means of data storage, and a device for detecting biomarkers, wherein the system is able to implement the method of toxicological screening according to claim 15.

* * * * *